US00PP36963P2

(12) United States Plant Patent
Snijder

(10) Patent No.: US PP36,963 P2
(45) Date of Patent: Sep. 16, 2025

(54) ***PELARGONIUM* PLANT NAMED 'PEQZ0104'**

(50) Latin Name: ***Pelargonium* x interspecific**
Varietal Denomination: PEQZ0104

(71) Applicant: SYNGENTA CROP PROTECTION AG, Basel (CH)

(72) Inventor: Ronald Christiaan Snijder, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 321 days.

(21) Appl. No.: 18/223,080

(22) Filed: Jul. 18, 2023

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 5/0277
See application file for complete search history.

*Primary Examiner* — Kent L Bell
(74) *Attorney, Agent, or Firm* — Dale Skalla

(57) ABSTRACT

A new *Pelargonium* plant named 'PEQZ0104' particularly distinguished by light rose colored inflorescences with a large vivid red spot in the middle of the floret, held above medium green foliage, on a mounding plant.

1 Drawing Sheet

Latin name of the genus and species of the plant claimed: *Pelargoniumx* interspecific.

Varietal denomination: 'PEQZ0104'.

BACKGROUND OF THE NEW PLANT

The present invention comprises a new *Pelargonium*, botanically known as *Pelargonium* interspecific, and hereinafter referred to by the variety name 'PEQZ0104'.

'PEQZ0104' is a product of a planned breeding program. The new cultivar 'PEQZ0104' has light rose colored inflorescences with a large vivid red spot in the middle of the floret, held above medium green foliage, on a mounding plant 'PEQZ0104' originates from a hybridization in a controlled breeding program made in July 2020 in a greenhouse in Gilroy, California. The female parent was a patented plant of *P.* x interspecific parentage identified as 'PECZ0003', U.S. Plant Pat. No. 23,509, with a smaller habit when compared to 'PEQZ0104'.

The male parent of 'PEQZ0104' was a patented, proprietary plant of *P.* x interspecific parentage, identified as 'PEQZ0017', U.S. Plant Pat. No. 28,711, with rose-colored florets when compared to 'PEQZ0104'. The resultant seed was sown in November 2020.

'PEQZ0104' was selected as one flowering plant within the progeny of the stated cross in May 2021 in a greenhouse in Gilroy, California.

The first act of asexual reproduction of 'PEQZ0104' was accomplished when vegetative cuttings were propagated from the initial selection in June 2021 in a greenhouse in Gilroy, California.

BRIEF SUMMARY OF INVENTION

Horticultural examination of plants grown from cuttings of the plant initiated in July 2021 in Gilroy, California and continuing thereafter, has demonstrated that the combination of characteristics as herein disclosed for 'PEQZ0104' are firmly fixed and are retained through successive generations of asexual reproduction.

'PEQZ0104' has not been observed under all possible environmental conditions. The phenotype may vary significantly with variations in environment such as temperature, light intensity, and day length.

A Plant Breeder's Right for this cultivar has not yet been applied for. 'PEQZ0104' has not been made publicly available prior to the effective filing date of this application, notwithstanding any disclosure that may have been made less than one year prior to the effective filing date of this application by the inventor or another who obtained 'PEQZ0104' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0104' with colors being as true as possible with an illustration of this type.

Figure 1:
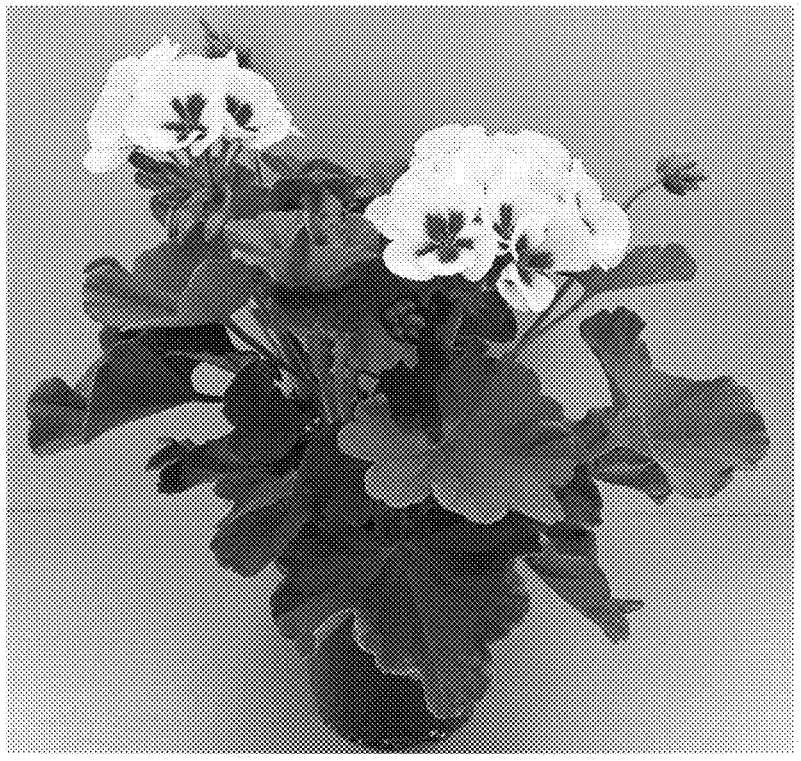
Figure 2:
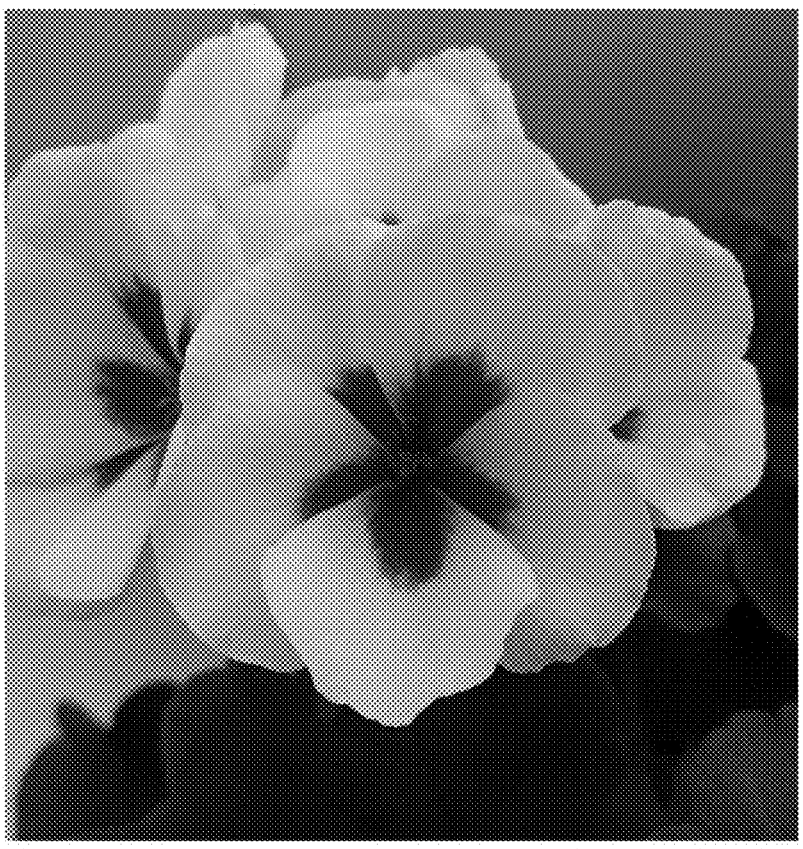

The photographic drawings show in FIG. 1, one flowering plant of the new variety and in FIG. 2, a close-up of an inflorescence.

DETAILED BOTANICAL DESCRIPTION

The plant descriptions and measurements were taken in Gilroy, California in early July 2023 under natural light. These plants were approximately 16 weeks old and were grown in a 20 cm pots, in a greenhouse trial. The plants shown in the photographs were about 16 weeks old growing in a 12 cm pot in a greenhouse. The photographs were taken in May 2023.

Color references are made to The Royal Horticultural Society Colour Chart (R.H.S.) of 2015.

TABLE 1

DIFFERENCES BETWEEN THE NEW VARIETY 'PEQZ0104' AND A MOST SIMILAR VARIETY

| | 'Tango White Splash' (not patented) | 'PEQZ0104' |
|---|---|---|
| Color upper surface of mature leaf: | Dark green, RHS 137A | Green, between RHS NN137A and RHS NN137B |
| Pedicel color: | Greyed red, RHS 178B | Greyed-orange RHS 177A upper section, fading to RHS 144A at the bottom section |

Plant:
- *Form, growth and habit.*—Mounding growth habit.
- *Plant height.*—18-21 cm.
- *Plant height (inflorescence included).*—28-31 cm.
- *Plant width.*—39-43 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Variegation.*—Absent.
- *Immature leaf, color upper surface.*—RHS 137B.
- *Immature leaf, lower surface.*—RHS 137D.
- *Mature leaf, color upper surface.*—Between RHS NN137A and RHS NN137B.
- *Mature leaf, color lower surface.*—Closest to RHS 137B.
- *Length.*—5.5-6 cm.
- *Width.*—8-10 cm.
- *Shape.*—Cordate.
- *Base shape.*—Cordate.
- *Sinus of mature leaf.*—Wide.
- *Leaf base openness.*—Variable, immature leaves wide open, mature leaves open.
- *Apex shape.*—Acute.
- *Margin.*—Slightly dentate.
- *Texture upper side.*—Hirsute.
- *Texture lower side.*—Hirsute.
- *Leaf zonation color.*—None.
- *Color of veins, upper surface.*—Between RHS NN137A and RHS NN137B.
- *Color of veins, lower surface.*—RHS 137C, distinct.
- *Pattern of veining.*—Palmate.
- *Petiole color.*—RHS 144B.
- *Petiole length.*—4.5-6 cm.
- *Diameter of petiole.*—0.2-0.3 cm.
- *Texture.*—Pilose, hirsute, glandular hairs.

Stem:
- *Quantity of branches.*—5-9.
- *Color of stem.*—Close to RHS 143B.
- *Anthocyanin coloration of stem.*—Little to no anthocyanin coloration.
- *Length of stem.*—9-20 cm.
- *Diameter.*—0.5 cm.
- *Length of internodes.*—1-4 cm.
- *Texture.*—Sparsely hirsute, pilose, glandular hairs.

Peduncle:
- *Color of peduncle.*—RHS 143C.
- *Length of peduncle.*—13-17 cm.
- *Peduncle diameter.*—0.3-0.5 cm.
- *Texture.*—Hirsute, glandular hairs.
- *Anthocyanin coloration of peduncle.*—Little to no anthocyanin coloration.

Pedicel:
- *Color of pedicel.*—RHS 177A upper section, fading to RHS 144A bottom section.
- *Length of pedicel.*—2.2-3.0 cm.
- *Diameter of pedicel.*—0.15-0.2 cm.
- *Texture.*—Sparsely pilose, glandular hairs.
- *Pedicel swelling.*—Swelling was not observed.

Bud (just before opening):
- *Color.*—RHS 144A.
- *Length.*—1.2-1.6 cm.
- *Width.*—0.4-0.8 cm.
- *Shape.*—Elliptical.

Inflorescence:
- *Type.*—Umbel; semi-spherical or nearly semi- spherical.
- *Lastingness of individual flowers.*—7-9 days at 18° C. temperature.
- *Number of inflorescences per plant.*—6-12, with 5-12 immature umbels in various stages.
- *Average total number of buds.*—18.
- *Fragrance.*—None.
- *Umbel diameter.*—7-10 cm.
- *Umbel depth.*—7-8 cm.

Corolla:
- *Form.*—Single.
- *Number of petals.*—5.
- *Diameter of flower.*—4.5-5.2 cm.
- *Depth of flower.*—1-2 cm.
- *Side view shape.*—Concave.
- *Color upper petals, upper surface.*—RHS 69B.
- *Color upper petals, lower surface.*—RHS 62C.
- *Length of upper petals.*—2.8-3.0 cm.
- *Width of upper petals.*—2.1-2.3 cm.
- *Color lower petals, upper surface.*—RHS 69B.
- *Color lower petals, lower surface.*—RHS 62C.
- *Markings on upper petals.*—Yes, distinct red purple RHS 57A spot and red purple veins RHS 57A on lower half of upper petal.
- *Markings on lower petals.*—Yes, distinct red purple RHS 57A spot on lower half of lower petal.
- *Length of lower petals.*—2.1-2.3 cm.
- *Width of lower petals.*—2.0-2.2 cm.
- *Petal shape.*—Obovate to spathulate.
- *Apex shape.*—Rounded.
- *Margin.*—Entire.
- *Base.*—Attenuate.
- *Petal texture.*—Papillose on both surfaces.

Calyx:
- *Number of sepals.*—5.
- *Color of sepals.*—RHS 144A fading to RHS 152D while ageing.
- *Length of sepals.*—1.2-1.3 cm.
- *Width of sepals.*—0.2-0.4 cm.
- *Sepal shape.*—Lanceolate to linear.
- *Apex shape.*—Acute.
- *Margins.*—Mostly fused.

*Texture, upper surface*.—Glabrous.

*Lower surface*.—Glandular hairs, hirsute.

*Sepal flexing*.—Mostly unflexed sepals. The narrowest sepals might flex moderately.

Reproductive organs:

Gynoecium:

*Pistil*.—RHS 60B.

*Length*.—0.7 cm.

*Style color*.—RHS 60B.

*Style length*.—0.3 cm.

*Stigma color*.—RHS 75B.

*Ovary color*.—RHS 138B.

*Ovary length*.—0.4-0.5 cm.

*Ovary diameter*.—0.2 cm.

Androecium:

*Number of stamens*.—5 with 2 staminodes.

*Color of filaments*.—RHS 155D

*Length filaments*.—0.7 cm..

*Anther color*.—RHS 51B.

*Length of anthers*.—0.2 cm.

*Color of pollen*.—RHS 171B.

*Pollen amount*.—Scarce.

*Fertility/seed set*.—Has not been determined to date.

*Disease/pest resistance*.—Has not been determined to date.

What is claimed is:

1. A new and distinct variety of *Pelargonium* plant named 'PEQZ0104' substantially as illustrated and described herein.

* * * * *